United States Patent
De Haan

(10) Patent No.: US 11,045,146 B2
(45) Date of Patent: Jun. 29, 2021

(54) DEVICE, SYSTEM AND METHOD FOR DETERMINING A VITAL SIGN OF A SUBJECT

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 207 days.

(21) Appl. No.: 16/077,748

(22) PCT Filed: Feb. 24, 2017

(86) PCT No.: PCT/EP2017/054276
§ 371 (c)(1),
(2) Date: Aug. 14, 2018

(87) PCT Pub. No.: WO2017/148807
PCT Pub. Date: Sep. 8, 2017

(65) Prior Publication Data
US 2019/0038234 A1    Feb. 7, 2019

(30) Foreign Application Priority Data
Mar. 1, 2016   (EP) .................................. 16158005

(51) Int. Cl.
*A61B 5/1455* (2006.01)
*A61B 5/00* (2006.01)
(Continued)

(52) U.S. Cl.
CPC .......... *A61B 5/7214* (2013.01); *A61B 5/0205* (2013.01); *A61B 5/02416* (2013.01);
(Continued)

(58) Field of Classification Search
None
See application file for complete search history.

(56) References Cited

U.S. PATENT DOCUMENTS

| 6,083,172 A | 7/2000 | Baker |
| 2013/0271591 A1 | 10/2013 | Van Leest |

FOREIGN PATENT DOCUMENTS

| WO | 2014/140978 | 9/2014 |
| WO | 2017055218 | 4/2017 |

OTHER PUBLICATIONS

Moco, et al., "Ballistocardiographic artifacts in PPG imaging"; IEEE Transactions on Biomedical Engineering, Nov. 20, 2015.
(Continued)

*Primary Examiner* — Eric F Winakur
*Assistant Examiner* — Marjan Fardanesh

(57) ABSTRACT

The present invention relates to a device, system and method for determining a vital sign of a subject. To reduce the effects of subject motion, in particular of ballistocardiographic motion, the device comprises an input interface (30) for obtaining at least two radiation signals, each radiation signal being acquired from different skin regions of the subject by detecting radiation reflected from or transmitted through the respective skin region in response to irradiation, an extraction unit (31) for extracting photoplethysmography (PPG) signals from the obtained radiation signals to obtain at least one PPG signal per skin region, an evaluation unit (32) for determining first weights for said skin regions depending on the relative and/or absolute strength of fundamental frequency and/or one or more harmonics in the spectrum of the PPG signal of the respective skin region, a combination unit (33) for combining two or more PPG signals of different skin regions based on their respective first weights to obtain a
(Continued)

combined PPG signal, and a vital sign determination unit (34) for deriving a vital sign from the combined PPG signal.

14 Claims, 4 Drawing Sheets

(51) Int. Cl.
 *A61B 5/024* (2006.01)
 *A61B 5/0205* (2006.01)
 *A61B 5/11* (2006.01)
(52) U.S. Cl.
 CPC .......... *A61B 5/1102* (2013.01); *A61B 5/1128* (2013.01); *A61B 5/14551* (2013.01); *A61B 5/7207* (2013.01); *A61B 5/7278* (2013.01)

(56) References Cited

OTHER PUBLICATIONS

Verkruysse et al., "Remote plethysmographic imaging using ambient light", Optics Express, 16(26), Dec. 22, 2008, pp. 21434-21445.
De Haan, et al., "Robust pulse-rate from chrominance-based rPPG", IEEE Transactions on Biomedical Engineering, vol. 60, No. 10, Oct. 2013, pp. 2878-2886.
De Haan, et al., "Improved motion robustness of remote-PPG by using the blood volume pulse signature", Physiol. Meas. 35 1913, 2014.
Nguyen, et al., "Spectrum-Averaged Harmonic Path (SHAPA) Algorithm for Non-Contact Vital Sign Monitoring with Ultra-wideband (UWB) Radar"; Conf Proc IEEE Eng Med Biol Soc., 2014, pp. 2241-2244.
Guha Balakrishnan, "Analyzing Pulse From Head Motions in Video"; Massachusetts Institute of Technology 2014.

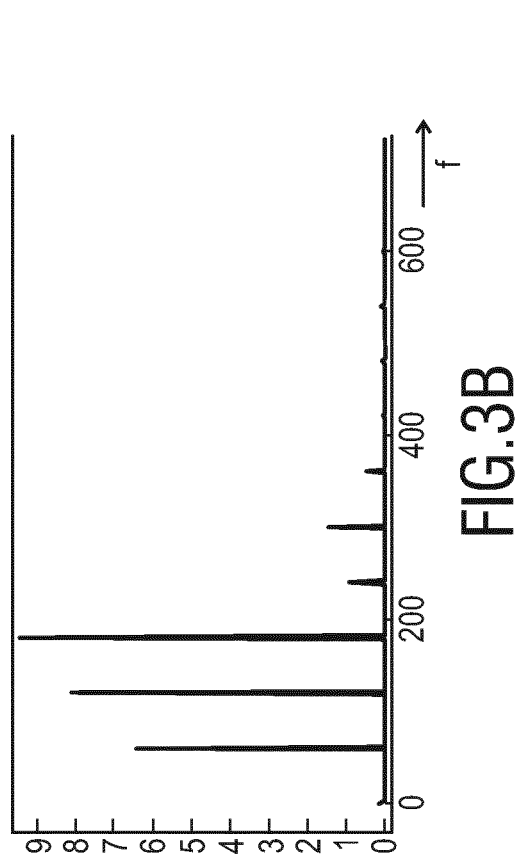
FIG.3A
FIG.3B
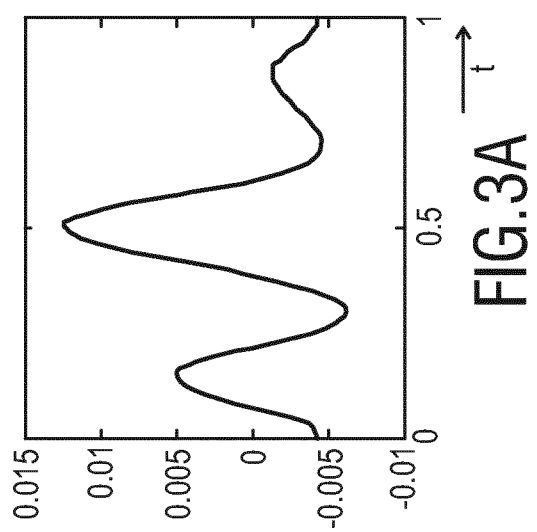
FIG.4A
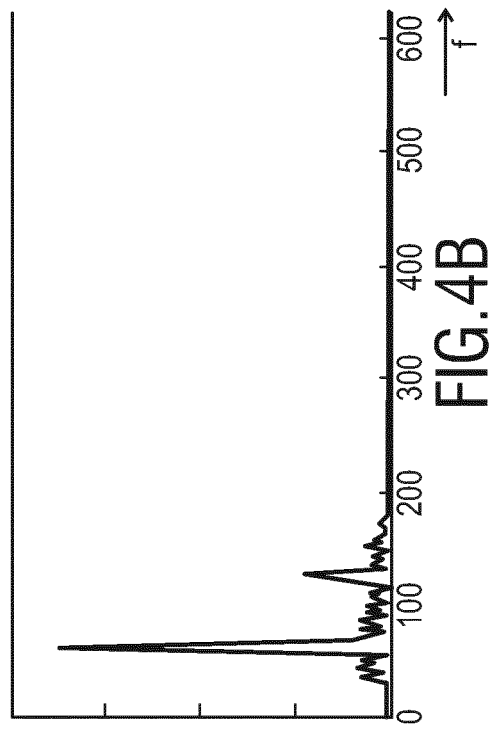
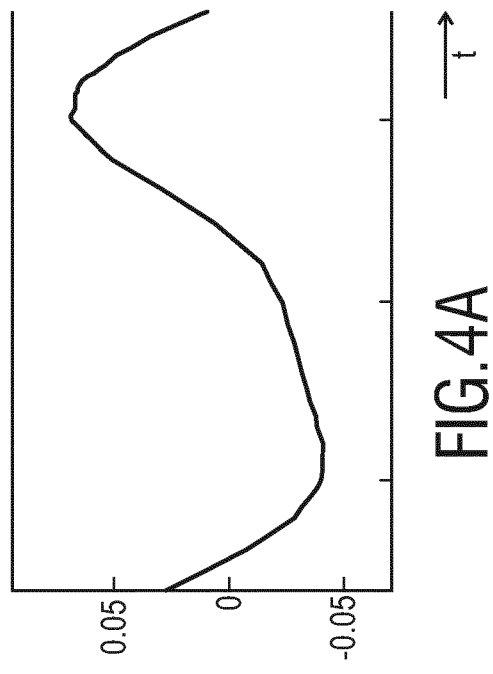
FIG.4B

DEVICE, SYSTEM AND METHOD FOR DETERMINING A VITAL SIGN OF A SUBJECT

CROSS REFERENCE TO RELATED APPLICATIONS

This application is the U.S. National Phase application under 35 U.S.C. § 371 of International Application No. PCT/EP2017/054276, filed Feb. 24, 2017, published as WO 2017/148807 on Sep. 8, 2017, which claims the benefit of European Patent Application Number 16158005.5 filed Mar. 1, 2016. These applications are hereby incorporated by reference herein.

FIELD OF THE INVENTION

The present invention relates to a device, system and method for determining a vital sign of a subject.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen (or other blood gasses/substances) saturation can be determined.

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin, premature babies, or patients with extensive burns.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

A major problem with known devices and methods is their sensitivity to subject motion. Remote PPG, e.g. for determining SpO2, aims to measure the modulation amplitude of the light reflected from the skin into a camera due to the varying blood volume in the skin. However, motion with respect to the light source also modulates the reflected light. Consequently, an rPPG camera captures the summed effect of motion and changes in blood volume (PPG). Band-pass filters and correlation-based approaches are typically used to reduce the motion-component in an rPPG signal, but this is not effective if the motion relates to the cardiac activity itself. This subject motion due to cardiac activity is generally referred to as ballistocardiographic (BCG) (micro)-motion and can be measured as variation of reflected light, with different strength at substantially every skin-region.

WO 2014/140978 A1 discloses a device for obtaining vital sign information of a subject comprising a first detection unit for acquiring first set of detection data allowing the extraction of a first vital sign information signal related to a first vital sign of the subject, a second detection unit for acquiring a second set of detection data allowing the extraction of a second vital sign information signal related to a second vital sign of the subject, an analysis unit for extracting the first vital sign information signal from the first set of detection data and for extracting the second vital sign information signal from the second set of detection data, a processing unit for combining the first vital sign information signal and the second vital sign information signal to obtain a combined vital sign information signal, and an extracting unit for extracting at least one of the first and second vital signs of the subject from the combined vital sign information signal.

A. V. Moço, S. Stuijk and G. de Haan, "Ballistocardiographic Artifacts in PPG Imaging," in IEEE Transactions on Biomedical Engineering, vol. 63, no. 9, pp. 1804-1811, September 2016 discloses a modeling of the amplitude of BCG-artifacts for a Lambertian surface illuminated by a light source. To derive peak-to-peak head displacements for the model, PPG and inertial sensor data were recorded at the pulse and cranial vertex. The effect of light source location at a mesh representation of a human face was simulated.

SUMMARY OF THE INVENTION

It is an object of the present invention to provide a device, system and method for determining a vital sign of a subject with increased accuracy and reliability, in particular with reduced disturbance by subject motion, especially BCG motion.

In a first aspect of the present invention a device for determining a vital sign of a subject related to pulse and/or a blood gas component is presented comprising an input interface for obtaining at least two radiation signals, each radiation signal being acquired from different skin regions of the subject by detecting radiation reflected from or transmitted through the respective skin region in response to irradiation, an extraction unit for extracting photoplethysmography, PPG, signals from the obtained radiation signals to obtain at least one PPG signal per skin region, an evaluation unit for determining first weights for said skin regions depending on the relative and/or absolute strength of fundamental frequency and/or one or more harmonics in the spectrum of the PPG signal of the respective skin region, a combination unit for combining two or more PPG signals of different skin regions based on their respective first weights to obtain a combined PPG signal, and a vital sign determination unit for deriving a vital sign from the combined PPG signal.

In a further aspect of the present invention a system for determining a vital sign of a subject is presented comprising a detector for acquiring at least two radiation signals, each radiation signal being acquired from different skin regions of the subject by detecting radiation reflected from or transmitted through the respective skin region in response to irradiation, and a device as disclosed herein for determining a vital sign of a subject based on the acquired radiation signals of the scene.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed system, in particular as defined in the dependent claims and as disclosed herein.

The present invention is based on the idea to recognize skin regions significantly suffering from BCG motion and reduce their contribution to the measurement, increasing the contribution from skin regions that exhibit low BCG motion. The discrimination is possible even though the pulse and BCG motion have the same fundamental frequency (pulse rate) since it has been found that the spectrum of the BCG motion has much stronger harmonics than the blood volume changes of the actual PPG signal. Hence, according to the present invention, the (relative and/or absolute) strength of the fundamental frequency and/or one or more harmonics is evaluated to find skin regions which exhibit (or suffer from) stronger subject motion, in particular BCG motion, than other skin regions. The contribution of those skin regions to the final measurement is reduced compared to the contribution from skin regions that exhibit lower subject motion, in particular BCG motion.

While the present invention is mainly directed to reducing the effect of BCG motion, it may also be useful in the reducing of other motion effects, which particularly have the same or rather similar fundamental frequency than the pulse. This may e.g. be body motion of the subject's body or motion of the light source.

Thus, the proposed device, system and method has increased robustness to movements of the subject, which is currently one of the main challenges. The present invention thus achieves motion robust vital sign measurement, e.g. SpO2 measurements, particularly from images acquired with a camera using rPPG technology, but also the measurement of other blood-(gas)-components may be improved with the same technique, such as CO, CO2, bilirubin, glucose, etc. Further, the present invention can generally be applied to optical contact PPG sensors, e.g. SpO2 sensors, using radiation (e.g. IR light and red light) reflected from or transmitted through a respective skin region. For instance, the measurements of several of such sensors can be weighted based on the evaluation of the measurements with respect to the strength of the fundamental frequency and/or one or more harmonics.

In an embodiment said combination unit is configured to weight each PPG signal with the first weight determined for the respective skin region and to sum the weighted PPG signals. This provides as rather simple but effective way of combining the weighted PPG signals. However, other combinations are possible, e.g. a weighted averaging, suppression of PPG signals having a first weight below a threshold, etc.

In another embodiment said evaluation unit is configured to determine said first weights for said skin regions depending on the relative and/or absolute strength of the fundamental frequency and first and/or second harmonics in the spectrum of the PPG signal of the respective skin region. Particularly the relative strength of fundamental and first harmonic of the pulse frequency shows the effect useful for determining the weights. If radiation signals for more than one wavelength (or wavelength channel) are obtained, the weights given to each sub-region may be the same for all wavelengths (or wavelength channels). This case is often preferred, e.g. the $SpO_2$ can be obtained from the similarly combined regions in two wavelength channels.

The evaluation unit may further be configured to determine a lower first weight for a first skin region having stronger harmonics (particularly as compared to the fundamental frequency) in the spectrum of the PPG signal of said first skin region than for a second skin region having weaker harmonics in the spectrum of the PPG signal of said second skin region. This further improves the suppression of motion artifacts.

In another embodiment the input interface is configured to obtain, per skin region, at least two radiation signals at different wavelength channels, said extraction unit is configured to extract a PPG signal per radiation signal and to combine, per skin region, said PPG signals of the different wavelength channels to obtain a region-combined PPG signal per skin region, and said evaluation unit is configured to use said region-combined PPG signals for determining the weights for said skin regions depending on the relative and/or absolute strength of the fundamental frequency and/or one or more harmonics in the spectrum of said region-combined PPG signal of the respective skin region. Hereby, a region-combined PPG signal may be obtained for a particular skin region as a weighted average of the PPG signals of the different wavelength channels extracted from the radiation signals obtained for said skin region. This further increases robustness of the obtained vital signs.

The extraction unit may further be configured to compute second weights for use in said weighted averaging using a normalized blood volume pulse vector signature based method, a chrominance based method, a blind source separation method, a principal component analysis or an independent component analysis. Further robustness can be achieved by use of a normalized blood volume pulse vector signature based method adapted to the vital sign to be determined.

Still further, in this case, the combination unit may be configured to combine, per wavelength channel, said PPG signals of the different skin regions based on their respective first weights to obtain a wavelength-combined PPG signal per wavelength channel, wherein said vital sign determination unit is configured to derive a vital sign from the wavelength-combined PPG signals.

Thus, in this embodiment the spectrum of the PPG signals is analyzed for every sub-region and a weighted average PPG signal over all regions per wavelength may be computed giving sub-regions that exhibit strong harmonics of the pulse frequency a lower weight in the averaging process. Sub-regions preferably get the same weight in the average for the two wavelengths to make sure both combinations reflect the same weighted skin region.

In another embodiment said input interface is configured to obtain, per skin region, at least two radiation signals at different wavelength channels, said extraction unit is configured to extract a PPG signal per radiation signal, wherein said combination unit is configured to combine, per wavelength channel, said PPG signals of the different skin regions based on their respective first weights to obtain a wavelength-combined PPG signal per wavelength channel, and said vital sign determination unit is configured to derive a vital sign from the wavelength-combined PPG signals. This provides another option to increase robustness of the obtained vital signs.

As mentioned above, the present invention can generally be used with contact PPG sensors or, preferably, remote PPG sensors, such as a camera for acquiring image data. Hence, in an embodiment the input interface is configured to obtain image data comprising a time sequence of image frames, said image data including at least two image data portions from different skin regions of the subject, said image data portions representing said radiation signals.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
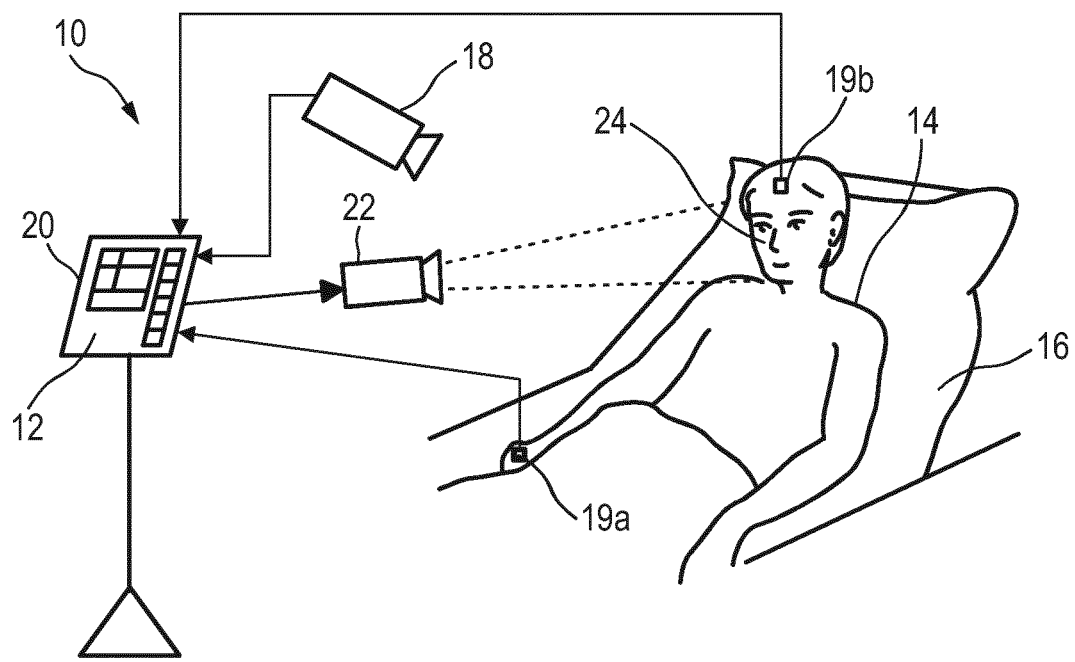
FIG. 1 shows a schematic diagram of a first embodiment of a system according to the present invention.

FIG. 1 shows a schematic diagram of a system 10 according to the present invention including a device 12 for extracting physiological information indicative of at least one vital sign of a subject 14 from detected electromagnetic radiation transmitted through or reflected from a subject. The subject 14, in this example a patient, lies in a bed 16, e.g. in a hospital or other healthcare facility, but may also be a neonate or premature infant, e.g. lying in an incubator, or person at home or in a different environment.

There exist different embodiments for a detector (also called signal acquisition unit) for detecting electromagnetic radiation transmitted through or reflected from a subject, which may alternatively (which is preferred) or together be used. In the embodiment of the system 10 two different embodiments of the detector are shown and will be explained below. Both embodiments of the detector are configured for deriving at least two detection signals (also called radiation signals) from the detected electromagnetic radiation, wherein each detection signal comprises wavelength-dependent reflection or transmission information in a different wavelength channel. Herby, optical filters used are preferably different, but can be overlapping. It is sufficient if their wavelength-dependent transmission is different.

In one embodiment the detector comprises a camera 18 (also referred to as imaging unit, or as camera-based or remote PPG sensor) including a suitable photosensor for (remotely and unobtrusively) capturing image frames of the subject 14, in particular for acquiring a sequence of image frames of the subject 14 over time, from which photoplethysmography (PPG) signals can be derived. The image frames captured by the camera 18 may particularly correspond to a video sequence captured by means of an analog or digital photosensor, e.g. in a (digital) camera. Such a camera 18 usually includes a photosensor, such as a CMOS or CCD sensor, which may also operate in a specific spectral range (visible, IR) or provide information for different spectral ranges. The camera 18 may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least two groups of some image pixels each being representative of a different skin region of the subject, e.g. the forehead, the cheek, the throat, the hand, etc. Thereby, an image pixel may correspond to one photosensitive element of a photo-detector and its (analog or digital) output or may be determined based on a combination (e.g. through binning) of a plurality of the photosensitive elements.

In another embodiment the detector comprises two or more optical photoplethysmography sensors 19a, 19b (also referred to as contact PPG sensor(s)) configured for being mounted to different skin region of the subject 14 for acquiring photoplethysmography signals from the different skin regions, in the embodiment shown in FIG. 1 from the forehead and the right hand. The PPG sensor 19a may e.g. be designed in the form of a finger-clip (as conventionally used for measuring blood oxygen saturation) and the PPG sensor 19b may e.g. be designed in the form of a sticker (as e.g. used for measuring heart rate), just to name a few of all the possible embodiments. The PPG sensors 19a, 19b may also be designed in other forms and arranged at other skin regions of the body.

When using a camera 18 the system 10 may further optionally comprise a light source 22 (also called illumination source), such as a lamp, for illuminating a region of interest 24, such as the skin of the patient's face (e.g. part of the cheek or forehead), with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength ranges (e.g. green and red or infrared light, or light in a sufficiently large wavelength range covering at least two wavelength channels) may be detected and/or evaluated.

The device 12 is further connected to an interface 20 for displaying the determined information and/or for providing medical personnel with an interface to change settings of the device 12, the camera 18, the PPG sensors 19a, 19b, the light source 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called live style environments, such as fitness equipment, a wearable, a handheld device like a smartphone, or the like. The uni- or bidirectional communication between the device 12, the camera 18, the PPG sensors 19a, 19b and the interface 20 may work via a wireless or wired communication interface. Other embodiments of the present invention may include a device 12, which is not provided stand-alone, but integrated into the camera 18 or the interface 20.

Figure 2:
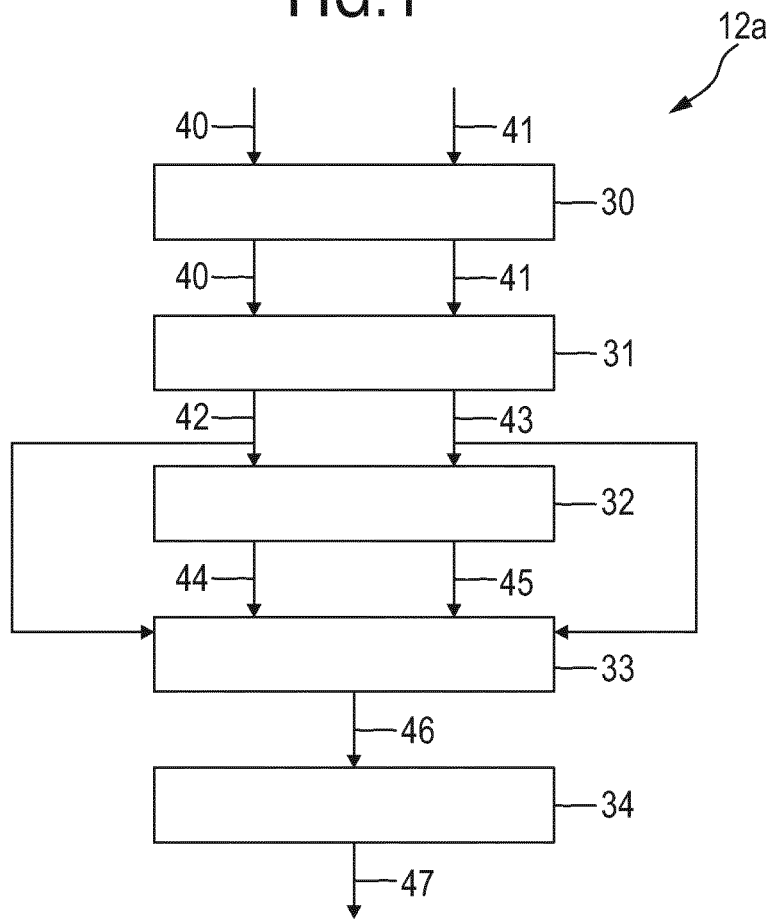
FIG. 2 shows a schematic diagram of a first embodiment of a device according to the present invention, FIGS. 3A and 3B respectively show a diagram of a PPG signal and its spectrum acquired from a skin region that is subject to BCG motion, FIGS. 4A and 4B respectively show a diagram of a PPG signal and its spectrum acquired from a skin region that is not subject BCG motion.

FIG. 2 shows a schematic diagram of a first embodiment of a device 12a according to the present invention, which may be used as device 12 in the system 10 shown in FIG. 1. The device 12a comprises an input interface 30 for obtaining at least two radiation signals 40, 41, each radiation signal being acquired from different skin regions (e.g. the forehead and the hand) of the subject 14 by detecting radiation reflected from or transmitted through the respective skin region in response to irradiation. An extraction unit 31 extracts PPG signals 42, 43 from the obtained radiation signals to obtain at least one PPG signal per skin region. An evaluation unit 32 determines first weights 44, 45 for said skin regions depending on the relative and/or absolute strength of fundamental frequency and/or one or more harmonics in the spectrum of the PPG signal of the respective skin region. A combination unit 33 combines two or more PPG signals 42, 43 of different skin regions based on their respective first weights 44, 45 to obtain a combined PPG signal 46. Finally, a vital sign determination unit 34 derives a vital sign 47 from the combined PPG signal 46, in particular in a conventional manner using the commonly known PPG technology.

The at least two radiation signals 40, 41 can be signals detected by different contact sensors, e.g. the contact sensors 19a, 19b shown in FIG. 1, or image signals representing different image areas of a common image data stream comprising a time sequence of image frames detected by the camera 18, said different image areas corresponding to different skin regions of the subject 14. Hereby, the different skin regions may be skin regions located at different parts of the body (e.g. forehead and hand, cheek and hand, etc.) or may be sub-regions of a common skin region, such as two (or more) spots on the cheek or on the forehead.

The present invention enables recognizing skin regions that are significantly suffering from BCG motion and reduce their contribution to the measurement, increasing the contribution from skin regions that exhibit low BCG motion. It is thereby exploited that the spectrum of the BCG motion has much stronger harmonics than the blood-volume changes of reflected in the PPG signals. This can be seen from a comparison of FIGS. 3A and 3B showing the BCG signal (FIG. 3A) in the reflected light from the face of a subject as well as the spectrum (FIG. 3B) and FIGS. 4A and 4B showing an rPPG signal (FIG. 4A) measured from a region of the face of a subject with little BCG motion as well as its spectrum (FIG. 4B). As can be seen in FIG. 3B (showing the signal amplitude over the frequency in bpm) the second harmonic of the pulse rate (which is 60 bpm in this example) has the highest amplitude, although the fundamental frequency is strong enough to interfere with the rPPG signal. As can be seen in FIG. 4B the fundamental frequency (i.e. the pulse rate) is strongest and the harmonics are significantly weaker.

Figure 5:
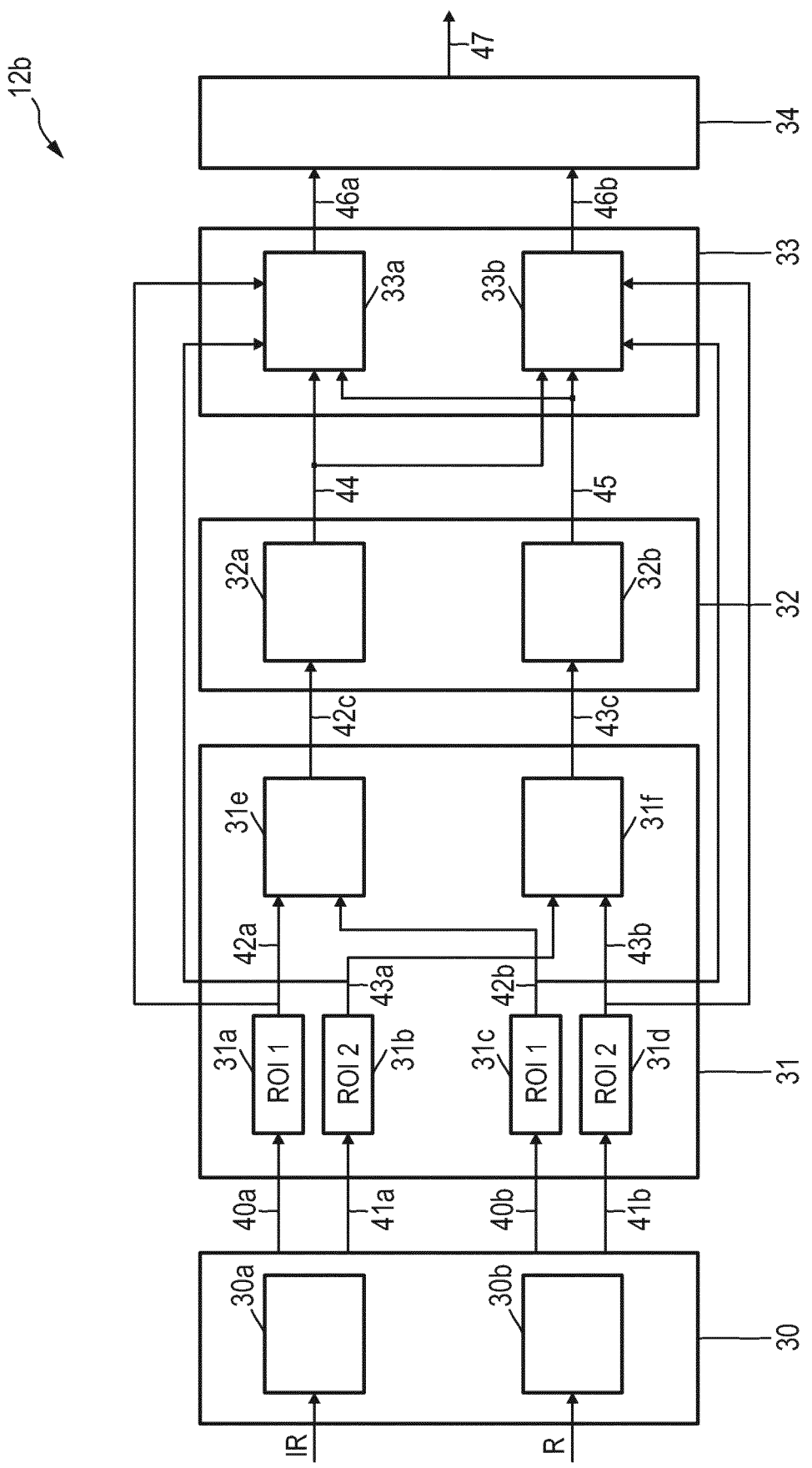
FIG. 5 shows a schematic diagram of second embodiment of device according to the present invention.

Another embodiment of the device 12b is shown in FIG. 5, which may be used for the following exemplary processing of and computation of an SpO2 value as vital sign. The SpO2 is computed as a ratio of relative pulsatilities in two (or more) wavelength intervals, e.g. 660 nm and 850 nm, i.e. from different wavelength channels received at the input sub-interfaces 30a (coupled e.g. to an infrared (IR) wavelength channel of the camera 18) and 30b (coupled e.g. to a red (R) (or another infrared) wavelength channel of the camera 18). Thus, if two different skin regions are taken into account in this embodiment, four radiation signals 40a, 40b, 41a, 41b are actually used (two wavelength channel per skin region for two skin regions). For the computation of the SpO2 the so-called ratio-of ratios method is applied as generally known and used in finger oximeters.

The skin region (ROI) seen by the camera is divided into at least two (preferably many more) sub-regions and the PPG signals for each sub-region for the wavelengths are computed. Thus, the extraction unit 31, comprising one extraction sub-unit 31a-31d per radiation signal, is configured to extract a PPG signal 42a, 42b, 43a, 43b per radiation signal. Further, combination sub-units 31e, 31f are provided to combine, per skin region, said PPG signals 42a, 42b, 43a, 43b of the different wavelength channels to obtain a region-combined PPG signal 42c, 43c per skin region.

The evaluation unit 32, which may comprise two evaluation sub-units 32a, 32b, is configured to use said region-combined PPG signals 42c, 42d for determining the weights 44, 45 for said skin regions depending on the relative and/or absolute strength of the fundamental frequency and/or one or more harmonics in the spectrum of said region-combined PPG signal 42c, 42d of the respective skin region.

Based on said weights 44, 45 the PPG signals 42a, 42b, 43a, 43c are combined in combination sub-units 33a, 33b of the combination unit 33 to obtain wavelength-combined PPG signal 46a, 46b per wavelength channel, from which e.g. the SpO2 as vital sign 47 is finally derived.

In a particular implementation of the device 12b a region-combined PPG signal for a particular skin region, e.g. the region-combined PPG signal 42c, is obtained by the respective combination sub-unit 31e, 31f as a weighted average of the PPG signals 42a, 42b of the different wavelength channels extracted from the radiation signals 40a, 40b obtained for said skin region. The extraction unit 31, in particular the combination sub-units 31e, 31f, may further be configured to compute second weights for use in said weighted averaging using a normalized blood volume pulse vector signature based method, a chrominance based method, a blind source separation method, a principal component analysis or an independent component analysis. The extraction unit 31 may particularly be configured to compute second weights for use in said weighted averaging using a normalized blood volume pulse vector signature based method adapted to the vital sign to be determined. Some explanations regarding said a normalized blood volume pulse vector signature based method and such other methods, which may be used for determining the second weights, shall be given in the following.

There exist several known methods to obtain a pulse signal S from (normalized) detection signals $C_n$, said methods being referred to as ICA, PCA, Pbv, CHROM, and ICA/PCA guided by Pbv/CHROM, which have also been described in the above cited paper of de Haan and van Leest. These methods can be interpreted as providing the pulse signal S as a mixture of different wavelength channels, e.g. red, green and blue signals from a color video camera, but they differ in the way to determine the optimal weighting scheme. In these methods the resulting weights are aimed at a mixture in which the distortions disappear, i.e. the "weighting vector" is substantially orthogonal to the main distortions usually caused by subject motion and/or illumination variations.

In the following some basic considerations with respect to the Pbv method shall be briefly explained.

The beating of the heart causes pressure variations in the arteries as the heart pumps blood against the resistance of the vascular bed. Since the arteries are elastic, their diameter changes in sync with the pressure variations. These diameter changes occur even in the smaller vessels of the skin, where the blood volume variations cause a changing absorption of the light.

The unit length normalized blood volume pulse vector (also called signature vector) is defined as Pbv, providing the relative PPG-strength in the red, green and blue camera signal. To quantify the expectations, the responses $H_{red}(w)$, $H_{green}(w)$, and $H_{blue}(w)$ of the red, green and blue channel, respectively, were measured as a function of the wavelength w, of a global-shutter color CCD cameral, the skin reflectance of a subject, $\rho_s(w)$, and used an absolute PPG-amplitude curve PPG(w). From these curves, shown e.g. in FIG. 2 of the above cited paper of de Haan and van Leest, the blood volume pulse vector $P_{bv}$ is computed as:

$$\vec{P}_{bv}^T = \begin{bmatrix} \dfrac{\int_{w=400}^{700} H_{red}(w)I(w)PPG(w)dw}{\int_{w=400}^{700} H_{red}(w)I(w)\rho_s(w)dw} \\ \dfrac{\int_{w=400}^{700} H_{green}(w)I(w)PPG(w)dw}{\int_{w=400}^{700} H_{green}(w)I(w)\rho_s(w)dw} \\ \dfrac{\int_{w=400}^{700} H_{blue}(w)I(w)PPG(w)dw}{\int_{w=400}^{700} H_{blue}(w)I(w)\rho_s(w)dw} \end{bmatrix}$$

which, using a white, halogen illumination spectrum I(w), leads to a normalized Pbv=[0.27, 0.80, 0.54]. When using a more noisy curve the result may be Pbv=[0.29, 0.81, 0.50].

The blood volume pulse predicted by the used model corresponds reasonably well to an experimentally measured normalized blood volume pulse vector, Pbv=[0.33, 0.77, 0.53] found after averaging measurements on a number of subjects under white illumination conditions. Given this result, it was concluded that the observed PPG-amplitude, particularly in the red, and to a smaller extent in the blue camera channel, can be largely explained by the crosstalk from wavelengths in the interval between 500 and 600 nm. The precise blood volume pulse vector depends on the color filters of the camera, the spectrum of the light and the skin-reflectance, as the model shows. In practice the vector turns out to be remarkably stable though given a set of wavelength channels (the vector will be different in the infrared compared to RGB-based vector).

It has further been found that the relative reflectance of the skin, in the red, green and blue channel under white illumination does not depend much on the skin-type. This is likely because the absorption spectra of the blood-free skin is dominated by the melanin absorption. Although a higher melanin concentration can increase the absolute absorption considerably, the relative absorption in the different wavelengths remains the same. This implies an increase of melanin darkens the skin, but hardly changes the normalized color of the skin. Consequently, also the normalized blood volume pulse $P_{bv}$ quite stable under white illumination. In the infrared wavelengths the influence of melanin is further reduced as its maximum absorption occurs for short wavelengths (UV-light) and decreases for longer wavelengths.

The stable character of Pbv can be used to distinguish color variations caused by blood volume change from variations due to alternative causes. The resulting pulse signal S using known methods can be written as a linear combination (representing one of several possible ways of "mixing") of the individual DC-free normalized color channels:

$$S = WC_n$$

with $WW^T=1$ and where each of the three rows of the 3×N matrix $C_n$ contains N samples of the DC-free normalized red, green and blue channel signals $R_n$, $G_n$ and $B_n$, respectively, i.e.:

$$\vec{R}_n = \frac{1}{\mu(\vec{R})}\vec{R} - 1, \vec{G}_n = \frac{1}{\mu(\vec{G})}\vec{G} - 1, \vec{B}_n = \frac{1}{\mu(\vec{B})}\vec{B} - 1.$$

Here the operator μ corresponds to the mean. Key difference between the different methods is in the calculation of the weighting vector W. In one method, the noise and the PPG signal may be separated into two independent signals built as a linear combination of two color channels. One combination approximated a clean PPG signal, the other contained noise due to motion. As an optimization criterion the energy in the pulse signal may be minimized. In another method a linear combination of the three color channels may be used to obtain the pulse signal. In still further methods, the ICA or the PCA may be used to find this linear combination. Since it is a priori unknown which weighted color signal is the pulse signal all of them used the periodic nature of the pulse signal as the selection criterion.

The Pbv method generally obtains the mixing coefficients using the blood volume pulse vector as basically described in US 2013/271591 A1 and the above cited paper of de Haan and van Leest. The best results are obtained if the band-passed filtered versions of $R_n$, $G_n$ and $B_n$ are used. According to this method the known direction of Pbv is used to discriminate between the pulse signal and distortions. This not only removes the assumption (of earlier methods) that the pulse is the only periodic component in the video, but also eliminates assumptions on the orientation of the distortion signals. To this end, it is assumed as before that the pulse signal is built as a linear combination of normalized color signals. Since it is known that the relative amplitude of the pulse signal in the red, green and blue channel is given by Pbv, the weights, $W_{PBV}$, are searched that give a pulse signal S, for which the correlation with the color channels $R_n$, $G_n$, and $B_n$ equals Pbv $$\vec{S}C_n^T = k\vec{P}_{bv} \Leftrightarrow \vec{W}_{PBV}C_nC_n^T = k\vec{P}_{bv}, \quad (1)$$

and consequently the weights determining the mixing are determined by $$\vec{W}_{PBV} = k\vec{P}_{bv}Q^{-1} \text{ with } Q = C_nC_n^T, \quad (2)$$

and the scalar k is determined such that $W_{PBV}$ has unit length. It is concluded that the characteristic wavelength dependency of the PPG signal, as reflected in the normalized blood volume pulse, Pbv, can be used to estimate the pulse signal from the time-sequential RGB pixel data averaged over the skin area. This algorithm is referred to as the $P_{bv}$ method.

Hence, as explained above, a pulse signal results as a weighted sum of the at least two detection signals $C_n$. Since all detection signals $C_n$ contain the pulse and different levels of (common) noise, the weighting (of the detection signals to obtain the pulse signal) can lead to a pure noise-free pulse. This is why ICA and PCA can be used to separate noise and pulse.

Thus, according to an embodiment of the present invention, the spectrum is computed and analyzed for every sub-region (i.e. every skin region) after first combining the PPG signals of the at least two wavelength channels into a more motion-robust pulse signal. This more robust pulse signal may result from any robust pulse-extraction method using multiple wavelengths, like e.g. PCA, ICA, ratio-of-two-wavelengths, blood-volume pulse signature-based, chrominance-based, etc. From the spectrum of the robust pulse signals from each sub-region a weight of that region is computed similarly as explained above, i.e. regions with high harmonic content get a reduced weight in the combination process. For instance, a weighted average PPG signal over all regions per wavelength may be computed giving sub-regions that exhibit strong harmonics of the pulse frequency a lower weight in the averaging process. Sub-regions preferably get the same weight in the average for the two wavelengths to make sure both combinations reflect the same weighted skin region. In other words, in that case the weights 44, 45 are determined using the spectrum of the robust PPG signals obtained as a weighted combination of signals from different wavelengths (e.g. using PCA, ICA, PBV-method, or CHROM, as explained above). The sub-region with the relatively lowest harmonic pulse energy receives the highest (first) weight in the combined region.

In another embodiment, the spectrum is computed from a pulse signal resulting from combining PPG signals from the wavelength channels using the blood-volume-pulse-signature-method, where the signature is adapted to the measured vital sign (e.g. SpO2).

Figure 6:
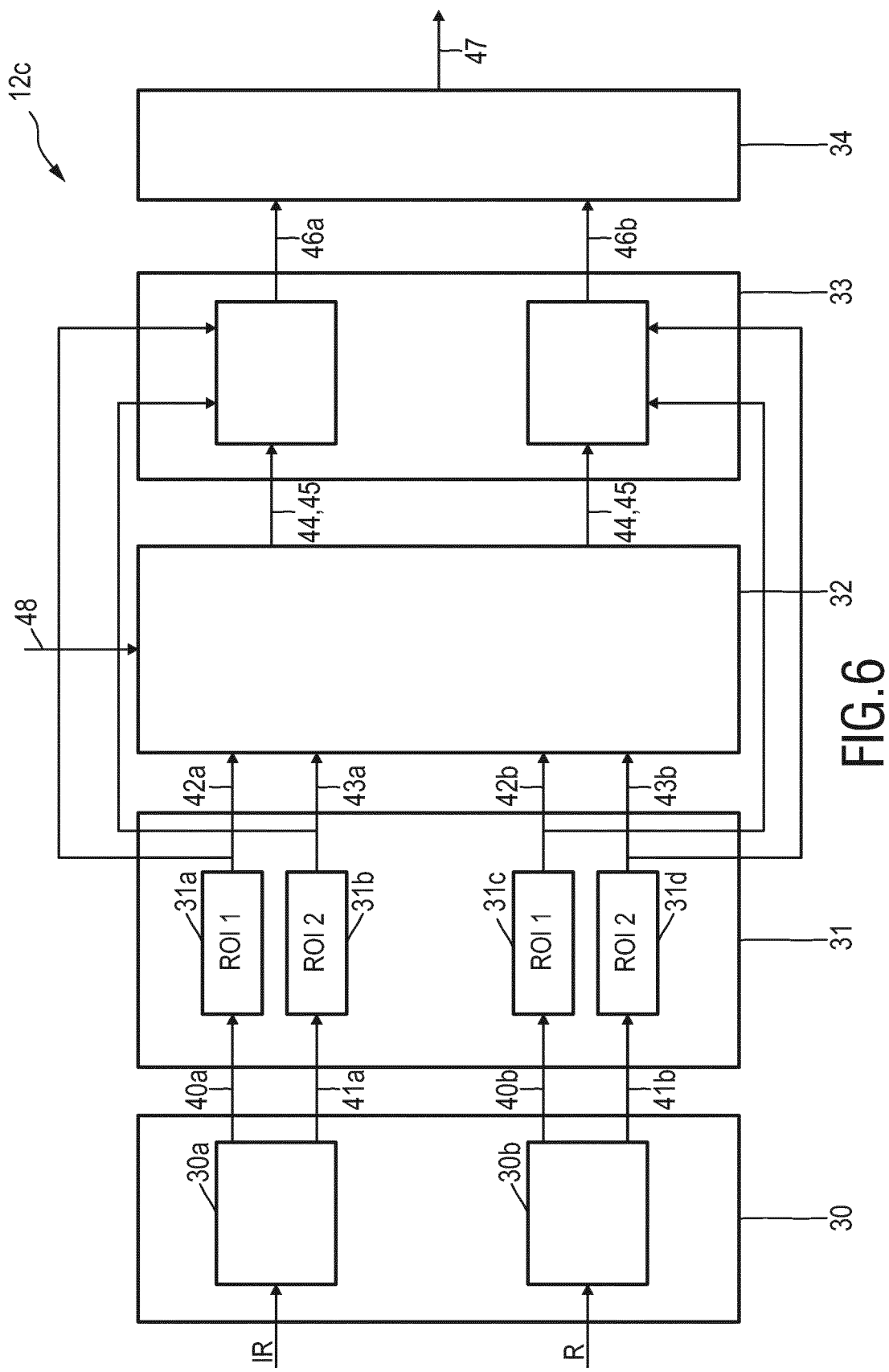
FIG. 6 shows a schematic diagram of third embodiment of device according to the present invention.

FIG. 6 shows a schematic diagram of third embodiment of device 12c according to the present invention. In this embodiment the combination unit 33 is again configured to combine, per wavelength channel, said PPG signals of the different skin regions based on their respective first weights 44, 45 to obtain a wavelength-combined PPG signal 46a, 46b per wavelength channel. The vital sign determination unit 34 then derives the vital sign 47 from the wavelength-combined PPG signals 46a, 46b. Furthermore, for determining the first weights 44, 45 additional information 48 is used in this embodiment. Said additional information 48 may e.g. be information about motion distortion (e.g. the relative strength of motion distortions) of the PPG signals 42a, 42b, 43a, 43b in the different skin regions, i.e. skin regions with less motion distortion should generally get a higher first weight than skin regions with more motion distortion. Such additional information 48 may be obtained from an external source, e.g. from motion detectors, or from motion analysis of the original radiation signals or images acquired over time representing the radiation signals or from which the radiation signals are derived.

The processing and the evaluation of the PPG signals 42a, 42b, 43a, 43b may be performed as explained above with respect to FIG. 5. However, other options may exist and be used. For instance, a preliminary first weight may be determined for each of the PPG signals 42a, 42b, 43a, 43b, and the preliminary first weights for PPG signals from the same ROI (e.g. for PPG signals 42a, 42b and for PPG signals 43a, 43b) may be averaged to obtain the first weights 44, 45 for the respective ROIs.

One application of the invention is the camera-based measurement of pulse-rate, respiration and SpO2 for patient monitoring. The contactless monitoring, with a camera, is assumed to be highly relevant for premature babies with very sensitive skin in NICUs, and for patients with damaged (e.g. burns) skin, but may also be more convenient than contact sensors as used in the general ward. However, the invention can also be used in other scenarios and with contact sensors (as alternatives or additions to the camera).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a vital sign of a subject related to pulse and/or a blood gas component, said device comprising:
    an input interface for obtaining at least two radiation signals, each radiation signal being acquired from different skin regions of the subject by detecting radiation reflected from or transmitted through the respective skin region in response to irradiation,
    an extraction unit for extracting photoplethysmography, PPG, signals from the obtained radiation signals to obtain at least one PPG signal per skin region,
    an evaluation unit for determining first weights for said skin regions depending on the relative and/or absolute strength of fundamental frequency and/or one or more harmonics in the spectrum of the PPG signal of the respective skin region, wherein said evaluation unit is configured to determine a lower first weight for a first skin region having stronger harmonics in the spectrum of the PPG signal of said first skin region than for a second skin region having weaker harmonics in the spectrum of the PPG signal of said second skin region,
    a combination unit for combining two or more PPG signals of different skin regions based on their respective first weights to obtain a combined PPG signal, and
    a vital sign determination unit for deriving a vital sign from the combined PPG signal.

2. The device as claimed in claim 1,
wherein said combination unit is configured to weight each PPG signal with the first weight determined for the respective skin region and to sum the weighted PPG signals.

3. The device as claimed in claim 1,
wherein said evaluation unit is configured to determine said first weights for said skin regions depending on the relative and/or absolute strength of the fundamental frequency and the first and/or second harmonics in the spectrum of the PPG signal of the respective skin region, in particular the relative strength of the fundamental frequency and the first harmonic.

4. The device as claimed in claim 1,
wherein said input interface is configured to obtain, per skin region, at least two radiation signals at different wavelength channels,
wherein said extraction unit is configured to extract a PPG signal per radiation signal and to combine, per skin region, said PPG signals of the different wavelength channels to obtain a region-combined PPG signal per skin region, and
wherein said evaluation unit is configured to use said region-combined PPG signals for determining the weights for said skin regions depending on the relative and/or absolute strength of the fundamental frequency and/or one or more harmonics in the spectrum of said region-combined PPG signal of the respective skin region.

5. The device as claimed in claim 4,
wherein said extraction unit is configured to obtain a region-combined PPG signal for a particular skin region as a weighted average of the PPG signals of the different wavelength channels extracted from the radiation signals obtained for said skin region.

6. The device as claimed in claim 5,
wherein said extraction unit is configured to compute second weights for use in said weighted averaging using a normalized blood volume pulse vector signature based method, a chrominance based method, a blind source separation method, a principal component analysis or an independent component analysis, in particular a normalized blood volume pulse vector signature based method adapted to the vital sign to be determined.

7. The device as claimed in claim 4,
wherein said combination unit is configured to combine, per wavelength channel, said PPG signals of the different skin regions based on their respective first weights to obtain a wavelength-combined PPG signal per wavelength channel, and
wherein said vital sign determination unit is configured to derive a vital sign from the wavelength-combined PPG signals.

8. The device as claimed in claim 1,
wherein said input interface is configured to obtain, per skin region, at least two radiation signals at different wavelength channels,
wherein said extraction unit is configured to extract a PPG signal per radiation signal,
wherein said combination unit is configured to combine, per wavelength channel, said PPG signals of the different skin regions based on their respective first weights to obtain a wavelength-combined PPG signal per wavelength channel, and
wherein said vital sign determination unit is configured to derive a vital sign from the wavelength-combined PPG signals.

9. The device as claimed in claim 1,
wherein said input interface is configured to obtain image data comprising a time sequence of image frames, said image data including at least two image data portions from different skin regions of the subject, said image data portions representing said radiation signals.

10. A system for determining a vital sign of a subject, said system comprising:
a detector for acquiring at least two radiation signals, each radiation signal being acquired from different skin regions of the subject by detecting radiation reflected from or transmitted through the respective skin region in response to irradiation, and
a device for determining a vital sign of a subject as defined in claim 1 based on the acquired radiation signals of the scene.

11. The system as claimed in claim 10,
wherein said detector comprises an imaging unit for acquiring image data comprising a time sequence of image frames, said image data including at least two image data portions from different skin regions of the subject, said image data portions representing said radiation signals.

12. The system as claimed in claim 10,
wherein said detector comprises at least two contact sensors for irradiating a respective skin region and for detecting radiation reflected from or transmitted through the respective skin region in response to said irradiation.

13. A method for determining a vital sign of a subject related to pulse and/or a blood gas component, said method being carried out by a device as claimed in claim 1 or by a computer or by a processor and comprising:
obtaining at least two radiation signals, each radiation signal being acquired from different skin regions of the subject by detecting radiation reflected from or transmitted through the respective skin region in response to irradiation,
extracting photoplethysmography, PPG, signals from the obtained radiation signals to obtain at least one PPG signal per skin region,
determining first weights for said skin regions depending on the relative and/or absolute strength of the fundamental frequency and/or one or more harmonics in the spectrum of the PPG signal of the respective skin region, wherein a lower first weight is determined for a first skin region having stronger harmonics in the spectrum of the PPG signal of said first skin region than for a second skin region having weaker harmonics in the spectrum of the PPG signal of said second skin region,
combining two or more PPG signals of different skin regions based on their respective first weights to obtain a combined PPG signal, and
deriving a vital sign from the combined PPG signal.

14. A non-transitory computer readable medium storing instruction which when executed by a processor cause a computer, when executed, to carry out the steps of the method as claimed in claim 13.

* * * * *